United States Patent [19]

Favetto et al.

[11] Patent Number: 4,834,017

[45] Date of Patent: May 30, 1989

[54] TIME-TEMPERATURE INTEGRATING INDICATOR FOR MONITORING THE COOKING PROCESS OF PACKAGED MEATS IN THE TEMPERATURE RANGE OF 85-100 DEGREES CELSIUS

[75] Inventors: Guillermo J. Favetto, Capital Federal; Jorge Chiriffe, Buenos Aires; Osvaldo C. Scorza, Buenos Aires; Carlos A. Hermida, Buenos Aires, all of Argentina

[73] Assignee: Frigorifico Rio Platense Saici Y F, Buenos Aires, Argentina

[21] Appl. No.: 32,313

[22] Filed: Mar. 30, 1987

[30] Foreign Application Priority Data

Mar. 13, 1987 [AR] Argentina ............................. 307005

[51] Int. Cl.⁴ ..................... G01N 33/12; G01N 21/78; G01K 11/12
[52] U.S. Cl. .................................. 116/207; 116/206; 116/216; 374/162; 426/88
[58] Field of Search ............... 116/206, 207, 219, 216; 426/87, 88; 374/161, 162; 422/57, 69

[56] References Cited

U.S. PATENT DOCUMENTS

| | | | |
|---|---|---|---|
| 3,888,631 | 6/1975 | Sturzinger | 426/88 X |
| 3,966,414 | 6/1976 | Khattab et al. | 426/88 X |
| 3,977,945 | 8/1976 | Tornmarck | 426/88 X |
| 3,999,946 | 12/1976 | Patel et al. | 426/88 X |
| 4,382,063 | 5/1983 | Romito et al. | 116/207 X |
| 4,388,332 | 6/1983 | Egee et al. | 116/216 X |
| 4,432,656 | 2/1984 | Allmendinger | 116/206 X |
| 4,459,046 | 7/1984 | Spirg | 116/216 X |
| 4,533,640 | 8/1985 | Shafer | 116/207 X |
| 4,601,588 | 7/1986 | Takahara et al. | 116/207 X |
| 4,643,588 | 2/1987 | Postle et al. | 374/162 X |
| 4,717,710 | 1/1987 | Shimizu et al. | 116/207 X |

Primary Examiner—John Petrakes
Attorney, Agent, or Firm—Ladas & Parry

[57] ABSTRACT

A time-temperature integrator based on color changes produced by the chemical reaction between reducing sugars and amino groups (i.e. amino-acids, peptides, proteins) permits the verification of the thermal history during cooking at 85°-100° C. of a hermetically sealed package for inspection and which can not be removed or substituted without breaking the package.

12 Claims, 1 Drawing Sheet

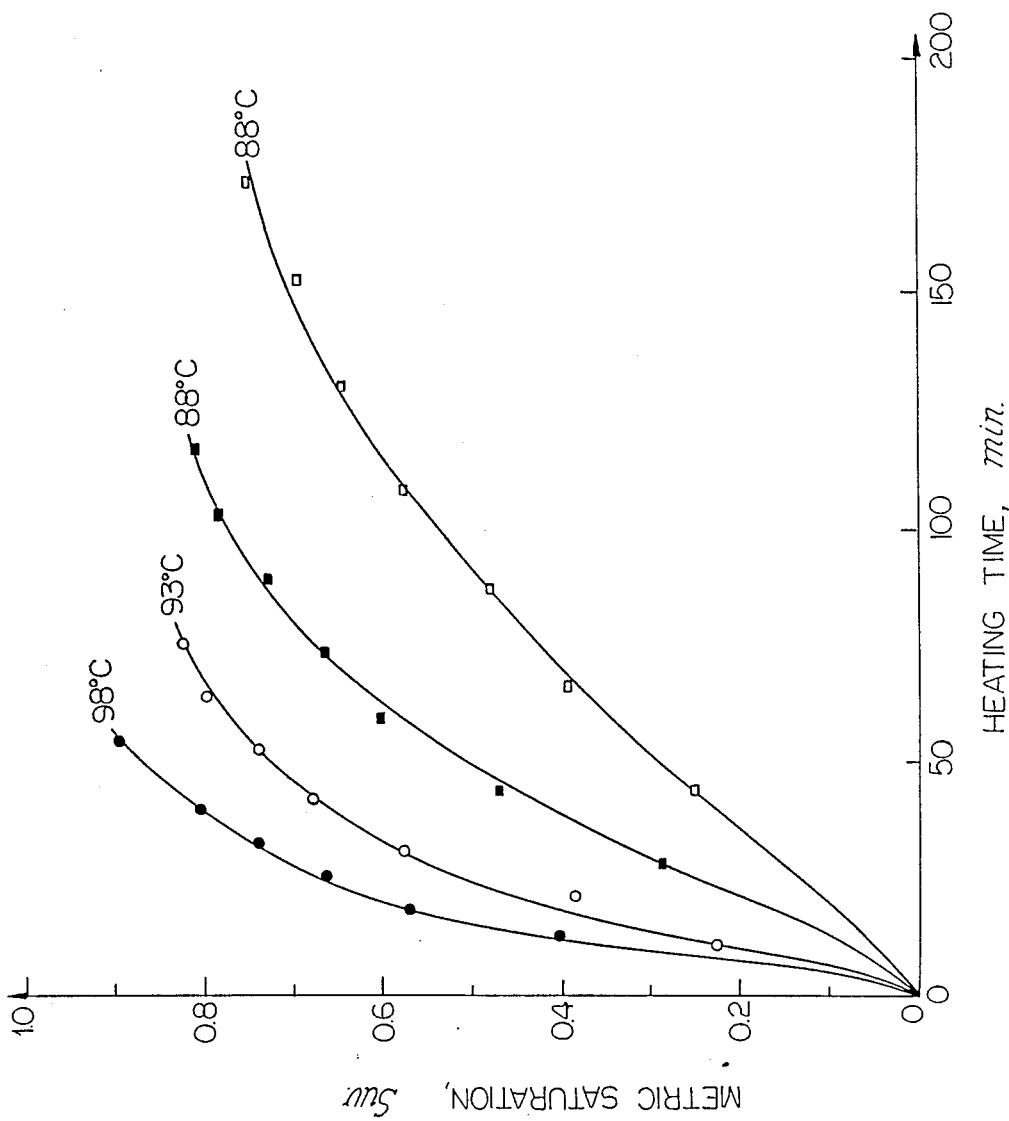

TIME-TEMPERATURE INTEGRATING INDICATOR FOR MONITORING THE COOKING PROCESS OF PACKAGED MEATS IN THE TEMPERATURE RANGE OF 85-100 DEGREES CELSIUS

BACKGROUND OF THE INVENTION

The temperature and the time at which a food (i.e. meat) has been cooked is very important from the point of view of health regulations. For instance, many international animal health regulations require that importation of meat from countries in which the foot and mouth disease virus is present, be restricted to meat which has been cooked at a combination of temperature and time sufficient to inactivate the virus. Therefore, it is important to monitor the temperature history of meats during the cooking process.

This invention relates to a time-temperature integrator indicator particularly suitable for meats (or meat products) which are cooked in hermetically sealed packages and permits the verification of the thermal history during cooking (at 85°–100° C.). without the need of opening the package for inspection. A time-temperature integrator is a device which registers a response according to the combined effect of time and temperature. In the present invention, the time-temperature integrator is based on color changes produced by the chemical reaction between reducing sugars and amino-acids, peptides or proteins, and usually known as the Maillard's reaction.

Methods currently accepted for monitoring the cooking process of meats for export in countries where the foot and mouth disease (FMD) (or other diseases) are endemic, are of a qualitative and subjective nature. At present, most meat exporters from countries where FMD virus is endemic rely upon the so-called "pink-juice test" which is highly subjective and can not be applied to meat pieces smaller than a cube of 1½ inch. It is relatively easy to determine the time-temperature conditions during cooking to inactivate the FMD virus in packaged meat pieces (cubes, ground, patties) or meat dishes. For a given package geometry, package size, physical-chemical characteristics of the product and heating method it is possible to find the time and temperature to inactivate the virus during cooking. However, what is more difficult is to have an objective method to verify that each single package of meat has been subjected to the time-temperature conditions required to inactivate the FMD virus. Most recently a system of temperature indicators (heat sensitive discs) which are suspended in the center of a bag of cooked beef (ground) was developed (Journal of Food Science, 47:388 (1982).

This type of temperature indicator shows color change when a pre-selected temperature is reached; this device provides no information concerning how long the system remained above the selected temperature, nor how far it rose above. This system permits food inspectors from import countries to verify that a given temperature has been reached in the "coldest" point of the package by opening it and checking the color of the indicator disc. Since this method requires opening the package it can not be applied to meat products individually packaged (i.e. one-portion cooked frozen meals). Under the system of inspection used in many meat-importers countries, upon arrival of an imported meat product, samples of the product are selected at random, ensuring that every carton of the product has the same chance of being inspected. This means that all meat packages must contain a temperature indicator device in its 'coldest' point. Obviously, this is not possible for small portions destined to the retail market since the temperature indicator (disc) will end up in the consumer's plate. Thus, the principle of temperature only indicators placed in the center of a meat package works only for packages which are to be opened for reprocessing after removal of the temperature sensitive device.

Instead of using a temperature indicator which registers the maximum internal temperature, we are proposing to use a time-temperature integrator indicator which is intimately fixed on the surface of the package (i.e. laminated inside the plastic film of a pouch) and can be inspected without opening the package, provided that the outer layer be transparent.

The color changing chemical integrator involves the reaction between reducing sugars and amino-acids, peptides or proteins, and is known as the Maillard's reaction. At the temperatures corresponding to cooking (85°–100° C.) Maillard's reaction quickly shows a series of colors between white and dark brown; the intensity of the color (as measured by reflectance or by visual comparison with a standard color chart) is proportional to the time and temperature of cooking. Whether the cooking times of meats (or meat formulations) in boiling water (i.e. 98°–00° C.) inactivate the FMD virus strongly depends (among other factors) on the size of the package; it could vary between 40 minutes to 3 hours. The rate of color change in the indicator can be preselected for any given coking range and package size by modifying the reactivity of the reducing sugar and/or the amino group, the pH of the medium or the concentration of the reactants. In this way the proper range of colors may be obtained for monitoring the cooking history of small or large meat packages (i.e. small or large cooking times).

SUMMARY OF THE INVENTION

The present invention involves the preparation of a solution containing a reducing sugar (i.e. xylose, glucose, fructose, lactose, maltose, etc) and an amino-acid (i.e. lysine, glucine, etc) peptide or protein, at a particular concentration and buffered to a given pH, incorporating this solution into a suitable thin support (i.e. filter paper) which is encapsulated in a moisture-proof plastic material and fixed by any means to the surface of the meat package or introduced between layers of a multilaminated packaging film. The concentration of the reducing sugar may vary between 5% by weight and 50% by weight; that of the amino group between 1% by weight, and 10% % by weight, and the pH between 3 and 9. Proper selection of these variables permits monitoring the thermal history of small or large meat packages during cooking.

In a demonstration of the present invention, filter paper (Whatman N 40) disks of 3 cm in diameter were soaked in a solution of fructose (30%) by weight), lysine (35% by weight) buffered at pH 7.0, removed from excess solution and hermetically sealed in a heat-resistant plastic film, such as high-density polyethylene.

The encapsulated indicators were then heated in water at 98° C., 95° C., 98° C., 95° C., 88° C. and 83° C. and the color function metric saturation ($S_{uv}$) at different times was measured by reflectance using a Hunter-Lab, Labscan Spectrocolorimeter. The results are shown in FIG. 1 which shows the sensitivity of color changes (as measured by the color function $S_{uv}$) to the combined effect of temperature and time. This data illustrates the suitability of the proposed indicator for developing a response (a color change) as a function of temperature and time at temperatures typical of meat cooking processes (i.e. 85°–100°0 C.).

As shown here, the combined effect of time and temperature on color changes can be put on a quantitative basis by measuring the color with a suitable instrument. However, the development of color in the heated indicator disks can also be detected visually since the disks go from color-less to dark brown. This will facilitate the inspection of meat packages.

In the case of long cooking times (i.e. 3 hours at 98° C.) such as those found in the tube cooking of meat (2–3 kg. of cubed or ground meat packaged in a plastic tube) fructose may be substituted by lactose (or other disaccharide) in the preparation of the indicator. Since lactose is a reducing sugar less reactive than fructose, color development proceeds slower, allowing one to obtain the proper range of colors for longer heating times.

Curves of color development similar to those shown in FIG. 1, but displaced in the time axis, were obtained when the fructose was substituted by lactose in the preparation of the indicator disk.

The following are examples which illustrate how the invention may be put into practice. All percentages are quoted by weight.

EXAMPLE 1

Disks of filter paper (Whatman No. 41) of 3 cm in diameter were soaked in a solution of fructose (30%) and lysine (3%), buffered at pH 7.0, removed from excess solution and hermetically sealed in envelopes of high-density polyethylene. Hungrian Goulash (452 g) containing 40% of meat (cubed in 1.5 cm size) and 60% of sauce was packaged in a rectangular plastic pouch (3 cm thickness). One indicator disk was intimately fixed at the upper surface of the pouch and the latter was cooked in a water bath at 98° C.+0.1° C. for 40 minutes. At this time the package was removed and rapidly cooled in cold water. The indicator disk was removed and the color function metric saturation ($S_{uv}$) was measured with a spectrocolorimeter. The value found was 0.809 which nearly corresponds (see FIG. 2) with the experimental heating time of 40 min (at 98° C.).

EXAMPLE 2

A disk of filter paper (3 cm in diameter) was soaked in a solution of lactose 18% and lysine (3%) buffered at pH 7.0, removed from excess solution and hermetically sealed in an envelope of high-density polyethylene. The indicator was then heat sealed at one end of a high-density polyethylene tube containing 2.8 kg of ground meat. The tube was then cooked in water at 98° C.+10° C. during 2 hours and 45 min., after which the tube was removed and rapidly cooled in cold water. The indicator disk was removed and the color measured with a spectrocolorimeter. The value observed was in good agreement with a previously determined standard color development curve.

In conclusion, using the present invention meat inspectors from import countries may easily verify the cooking history of meat packages by comparing the color of the time-temperature integrators fixed at the surface of the package or introduced between the layers of multilaminated packaging film, with a standard color chart. This inspection avoids the opening of the package which is required by systems which utilize solely temperature indicators placed in the 'coldest' point of the package.

Finally, it is important to note that the chemicals used in this time-temperature integrator (sugars, amino-acids, peptides or proteins) are absolutely safe since they are normal components of foods; thus any leakage or transfer from the indicator to the food would not constitute a danger to human health.

What is claimed is:

1. A time temperature integrator indicator for monitoring the cooking process of packaged meats in the temperature range 85° C. to 100° C., which comprises a porous carrier having incorporated by absorption a solution comprising a reducing sugar and one of the group consisting of an amino acid, peptide and protein; the indicator being sealed between two layers of moisture proof material; said indicator sealed between two layers of moisture proof material being intimately fixed by any means to the surface of a sealed moisture proof package containing meat or meat products.

2. The time temperature integrator indicator of claim 1, wherein the reducing sugar is selected from the group consisting of xylose, glucose, fructose, maltose and lactose.

3. The time-temperature integrator indicator of claim 1, wherein the amino acid is lysine or glycine.

4. The time-temperature integrator indicator of claim 1, wherein the pH of the impregnating solution is between 3 and 9.

5. A time temperature integrator indicator for monitoring the cooking process of packaged meats in the temperature range 85° C. to 100° C., which comprises a porous carrier having incorporated by absorption a solution comprising from 5 to 50% by weight of a reducing sugar and from 1 to 10% by weight of at least one member of the group consisting of an amino acid, a peptide and a protein; said indicator being sealed between two layers of moisture proof plastic material, said indicator being capable of being intimately fixed by any means to the surface of a package containing meat or meat products.

6. The time temperature integrator indicator of claim 5, wherein the reducing sugar is selected from the group consisting of xylose, glucose, fructose, maltose and lactose.

7. The time temperature indicator of claim 5 wherein the amino acid is lysine or glycine.

8. The time-temperature integrator indicator of claim 5, wherein the porous carrier is filter paper.

9. The time-temperature integrator indicator of claim 5, wherein the pH of the impregnating solution is between 3 and 9.

10. A time temperature integrator indicator for monitoring the cooking process of packaged meats in the temperature range 85° C. to 100° C., which comprises a filter paper carrier having incorporated by absorption a solution comprising from 5 to 50% by weight of a reducing sugar selected from the group consisting of xylose, glucose, fructose, maltose, and lactose, and from 1 to 10% by weight of an amino acid selected from the group consisting of lysine and glycine; said solution having a pH value from 3 to 9; the indicator being hermetically sealed between two layers of transparent moisture proof plastic material; said indicator being capable of being intimately fixed by any means to the surface of a package containing meat or meat products.

11. The indicator, as in claim 1 wherein the sealed moisture proof package is a plastic package.

12. The indicator, as in claim 11 wherein the indicator which is sealed within the moisture proof material is affixed to the surface of the package.

* * * * *